(12) United States Patent
van den Heuvel et al.

(10) Patent No.: US 7,836,750 B2
(45) Date of Patent: Nov. 23, 2010

(54) GAS DETECTION SYSTEM AND METHOD

(75) Inventors: Nils van den Heuvel, Amersfoort (NL); Hans van Schaik, Middelburg (NL)

(73) Assignee: Bruker Chemical Analysis, BV, Middleburg (NL)

( * ) Notice: Subject to any disclaimer, the term of this patent is extended or adjusted under 35 U.S.C. 154(b) by 447 days.

(21) Appl. No.: 11/986,210

(22) Filed: Nov. 20, 2007

(65) Prior Publication Data

US 2008/0121015 A1 May 29, 2008

(30) Foreign Application Priority Data

Nov. 23, 2006 (EP) .................................. 06256010

(51) Int. Cl.
*G01N 27/04* (2006.01)
*G01N 27/12* (2006.01)
*G01N 30/54* (2006.01)
*G01N 30/62* (2006.01)

(52) U.S. Cl. ...................... 73/23.4; 73/23.41; 73/23.42; 73/40

(58) Field of Classification Search ........................ None
See application file for complete search history.

(56) References Cited

U.S. PATENT DOCUMENTS

| | | | |
|---|---|---|---|
| 4,080,821 A * | 3/1978 | Johnston | 73/25.03 |
| 4,843,016 A | 6/1989 | Fine | |
| 5,591,406 A | 1/1997 | Hirai et al. | |
| 5,670,707 A | 9/1997 | Fennell et al. | |
| 5,830,353 A * | 11/1998 | Henderson | 210/198.2 |
| 5,859,360 A * | 1/1999 | Magni et al. | 73/19.05 |
| 5,938,817 A * | 8/1999 | Shibamoto et al. | 95/23 |
| 6,324,892 B1 * | 12/2001 | Nishina et al. | 73/23.2 |
| 2002/0182739 A1 | 12/2002 | Sadik et al. | |
| 2007/0151367 A1 * | 7/2007 | Hastings et al. | 73/861.77 |
| 2007/0224693 A1 * | 9/2007 | Prest | 436/161 |

FOREIGN PATENT DOCUMENTS

| | | |
|---|---|---|
| EP | 1 582 868 A1 | 10/2005 |
| JP | 05-346424 A * | 12/1993 |
| WO | WO 2005/108953 A2 | 11/2005 |

OTHER PUBLICATIONS

Grob, K., "Working Safely with Hydrogen as a Carrier Gas", Restek Advantage, vol. 2, 1998, pp. 1-3.*

* cited by examiner

*Primary Examiner*—Daniel S Larkin
(74) *Attorney, Agent, or Firm*—Law Office of Paul E. Kudirka

(57) ABSTRACT

An example of a gas detection system includes a gas chromatograph oven, a gas detector, a sample gas moving device, and a flow detector. An example of a method for detecting gas includes flowing a sample gas from the oven, determining whether the flow rate equals or is less than a minimum, and determining whether the concentration of a first gas of the sample gas, such as a combustible gas, equals or exceeds a maximum. If either the flow rate or the concentration indicates an error condition or is out of bounds, an alarm response is initiated. The alarm response may include shutting off the flow of the first gas to the oven, and flowing a second gas, such as a safe gas, to the oven.

20 Claims, 5 Drawing Sheets

GAS DETECTION SYSTEM AND METHOD

FIELD OF THE INVENTION

The present invention relates generally to gas detection, such as may be implemented in conjunction with gas chromatography, and the fail-safe operation of a system for implementing gas detection.

BACKGROUND OF THE INVENTION

Gas chromatography entails the analytical separation of a vaporized or gas-phase sample that is injected into a chromatographic column. The column is typically housed in a thermally controlled oven. A chemically inert carrier gas, such as hydrogen, helium or nitrogen, is typically utilized as the mobile phase for elution of the analyte sample in the column. The carrier gas is typically introduced into the column at a location near where the sample is injected, e.g., at the head of the column, and thus carries the sample through the column. The type of analyte detector employed with the gas chromatographic (GC) system often dictates the particular carrier gas utilized. Hydrogen is often a desirable choice for many GC systems for various reasons such as ensuring good sensitivity of the detector employed, such as a flame ionization detector (FID). Hydrogen, however, is a combustible gas with a lower explosion level (LEL) of 4% (40,000 ppm). While hydrogen diffuses rapidly in open air, GC ovens are airtight as well as thermally isolated. Accordingly, in the case of a hydrogen leak inside the GC oven, there is a risk that the hydrogen level may ramp up enough to cause an explosion.

In view of the foregoing, there is a need for a system for detecting leakage of combustible gases such as hydrogen in GC ovens, for enabling fail-safe operation of GC systems in which the use of a combustible gas as a GC carrier gas is desirable, and for preventing such leakage from causing a dangerous condition such as an explosion.

SUMMARY OF THE INVENTION

To address the foregoing problems, in whole or in part, and/or other problems that may have been observed by persons skilled in the art, the present disclosure provides apparatus, devices, systems and/or methods relating to proportional valves, as described by way of example in implementations set forth below.

According to one implementation, a gas detection system includes a gas chromatograph (GC) oven, a self-heating gas detector, a sample gas moving device interposed between the GC oven and the gas detector, and a flow detector. The flow detector includes circuitry for monitoring the self-heating of the gas detector.

According to another implementation, the gas detection system also includes a sample gas cooling device fluidly interposed between the GC oven and the sample gas moving device. The cooling device includes a condensation drain.

According to another implementation, a gas detection system includes a GC oven, a gas detector, a sample gas moving device interposed between the GC oven and the gas detector, and a flow detector. The system also includes means for receiving a flow measurement signal from the flow detector indicative of the flow rate of a sample gas flowing from the GC oven to the gas detector, and for determining whether the value of the flow measurement signal is less than or equal to a minimum flow rate value. The system further includes means for switching from flowing a first gas into the GC oven to flowing a second gas into the GC oven in response to the value of the flow measurement signal being less than or equal to the minimum flow rate value.

According to another implementation, a method for detecting a gas during a gas chromatographic (GC) process is provided. A sample gas is flowed from a GC oven. A determination is made as to whether a concentration of a first gas in the sample gas equals or exceeds a maximum gas concentration value. A determination is also made as to whether the flow rate of the sample gas equals or is less than a minimum flow rate value. If the first gas equals or exceeds the maximum gas concentration value, or if the flow rate equals or is less than the minimum flow rate value, an alarm response is initiated.

According to another implementation, the alarm response includes ceasing the flow of the first gas to the GC oven and flowing a second gas to the GC oven.

According to another implementation, the alarm response includes activating an alarm indicator.

Other apparatus, devices, systems, methods, features and/or advantages of the invention will be or will become apparent to one with skill in the art upon examination of the following figures and detailed description. It is intended that all such additional apparatus, devices, systems, methods, features and/or advantages be included within this description, be within the scope of the invention, and be protected by the accompanying claims.

DETAILED DESCRIPTION OF THE INVENTION

In general, the term "communicate" (for example, a first component "communicates with" or "is in communication with" a second component) is used herein to indicate a structural, functional, mechanical, electrical, optical, magnetic, ionic or fluidic relationship between two or more components or elements. As such, the fact that one component is said to communicate with a second component is not intended to exclude the possibility that additional components may be present between, and/or operatively associated or engaged with, the first and second components.

The subject matter disclosed herein generally relates to systems, apparatus, devices and methods related to gas detection, particularly in conjunction with gas chromatography (GC). Examples of implementations relating to the invention are described in more detail below with reference to FIGS. 1-6.

Figure 1:
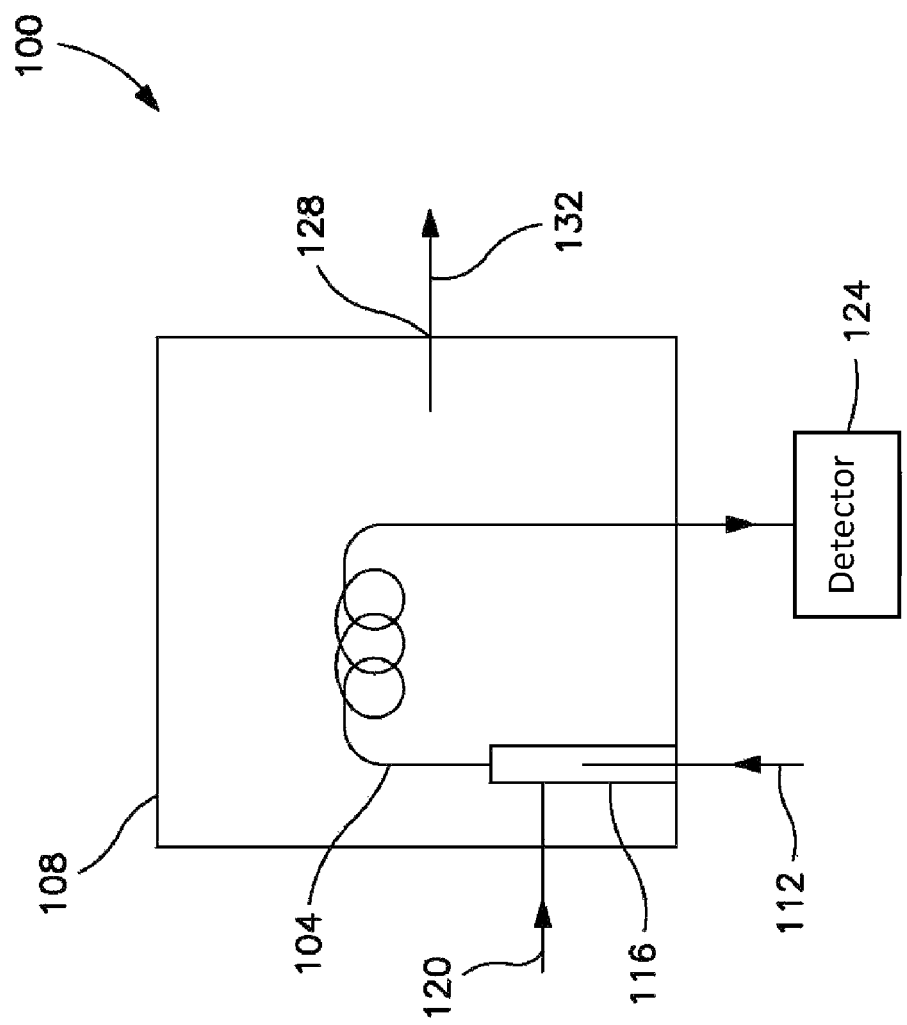
FIG. 1 is a schematic view of an example of a gas chromatographic system that may be employed in conjunction with the invention.

FIG. 1 schematically illustrates a few basic components of a gas chromatograph (GC) apparatus or system 100, as an example of the type of apparatus (or system) that may be utilized in conjunction with the invention. The GC apparatus 100 includes a chromatographic column 104 enclosed in an enclosure 108 often termed an oven. The column 104 may be of the packed or open tubular (capillary) type. A portion of the column 104 may be coiled to accommodate a desired length while minimizing the size of the GC oven 108. The oven 108 may be equipped with thermostating componentry (not shown) to precisely control the temperature of the column 104 (or the analyte sample in the column 104). Thermostasis may involve varying the temperature on a step-wise or continuous basis along a programmed temperature curve to balance parameters such as elution time and measurement resolution. A sample supply source or injection system 112 includes a syringe (not shown) or other fluid moving means to introduce liquid or gaseous analyte samples into the column 104 via an interface 116 such as a fitting mounted through the wall of the oven 108. Sample injection may be carried out on an automated, semi-automated, or manual basis. A carrier gas supply system establishes a flow of a carrier gas, such as hydrogen, helium or nitrogen, into the interface 116 through a carrier gas supply line 120 (e.g., a suitable conduit such as a tube or pipe) at a regulated flow rate and/or pressure. The injected analyte sample is transported by the carrier gas through the column 104, and exits to a downstream detection and data acquisition system generally and collectively represented by the schematic element 124. The detecting portion of the system 124 may include any detector suitable for analytical separation processes such as, for example, a flame ionization detector (FID), a thermal conductivity detector (TCD), an electron capture detector (ECD), a thermionic specific detector (TSD), a pulsed flame photometric detector (PFPD), etc. As appreciated by persons skilled in the art, a suitable electronic control system (not shown) may be utilized to control one or more of the operative components briefly described above. Moreover, variations, equivalents, substitutions, and further details of the operative components briefly described above are readily appreciated by persons skilled in the art, and thus need not be described further in this disclosure.

As also appreciated by persons skilled in the art, the GC apparatus 100 may have a multi-channel configuration. For example, the sample injection system 112 may include more than one sample injector, the oven 108 may include more than one column 104, and the detecting portion of the system 124 may include more than one detector. It is also understood that for simplicity, other components that may be included with the GC apparatus 100 such as, for example, a readout/display module, user input means such as a control console, network interfacing means, etc., are not shown but are readily known to persons skilled in the art.

As further illustrated in FIG. 1, the GC apparatus 100 includes a sample carrier gas outlet 128 communicating with a sample gas line 132. The interior of the GC oven 108 typically contains a gaseous mixture of air and other components. In undesirable cases, the gas in the oven 108 may include carrier gas, which may be the result of leakage from the column 104, interface 116, carrier gas supply line 120, or the like. Accordingly, the sample gas outlet 128 and gas line 132 are utilized to conduct sample gas, including any carrier gas that may be present within the confines of the oven 108, to a gas detection system as will now be described in conjunction with FIG. 2.

Figure 2:
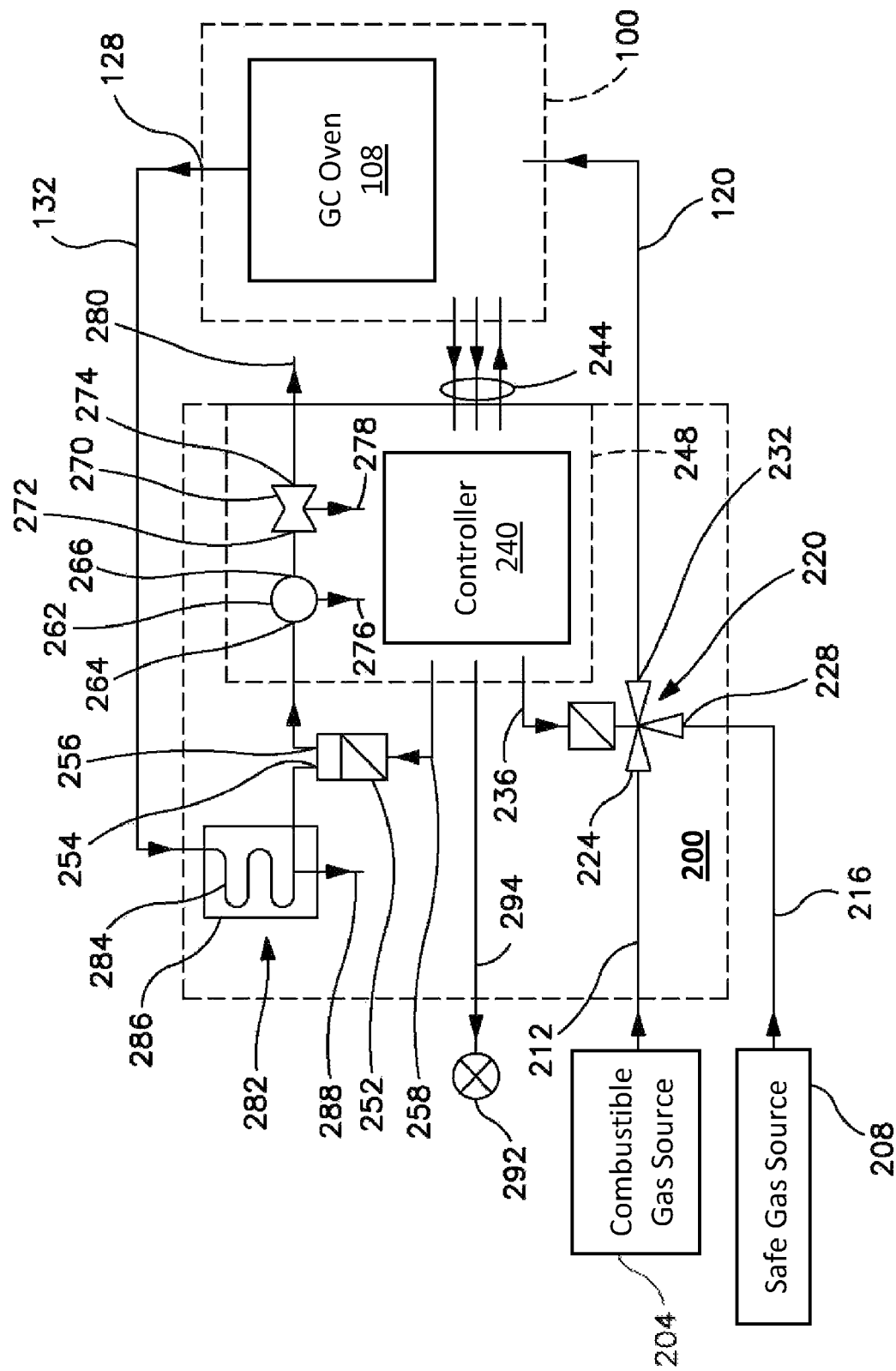
FIG. 2 is an elevation view of an example of a gas detection system according to one implementation of the invention.

FIG. 2 schematically illustrates an example of a gas detection system 200 interfaced with a GC apparatus, such as the GC apparatus 100 illustrated by example in FIG. 1, according to one implementation. Depending on the particular implementation, the gas detection system 200 may also be characterized as a gas leak protection system. A means is provided for supplying one or more combustible carrier gases such as, for example, hydrogen, to the GC system 100. A means is also provided for supplying one or more carrier gases typically considered safer (i.e., less combustible or non-combustible) for operation in the GC oven 108 such as, for example, helium and/or nitrogen. In the illustrated example, a combustible gas source 204 and a safe gas source 208 are provided, which may be separate devices or provided in a physically integrated module. The outlet of the combustible gas source 204 fluidly communicates with a combustible gas supply line 212 (e.g., a suitable conduit such as a tube or pipe), and the outlet of the safe gas source 208 fluidly communicates with a safe gas supply line 216. The combustible gas supply line 212 and the safe gas supply line 216 fluidly communicate with respective inlets of a gas selection or switching device 220. The gas selection device 220 may include any suitable selective gas routing means that typically provides inlets 224 and 228 for receiving the different carrier gases being supplied, and at least one outlet 232 for outputting the selected gas to the carrier gas supply line 120 that leads to the GC oven 108. One non-limiting example of a suitable gas selection device 220 is a selectable multi-port valve such as a solenoid-actuated valve.

The gas selection device 220 may be controlled via an electrical line 236 by a suitable electronic controller 240 such as, for example, a microcontroller, microprocessor, processor, application specific integrated circuit (ASIC), digital signal processor (DSP), computer (e.g., personal computer, networked client terminal, handheld computing device, etc.), or the like. The same electronic controller 240 may be utilized to communicate with other components of the gas detection system 200 to receive and/or send various types of signals such as data signals, measurement signals, and timing and control signals. In addition, the electronic controller 240 may communicate with the GC system 100 via a suitable GC interface 244 to implement various GC-related functions appreciated by persons skilled in the art. The electronic controller 240 and GC interface 244 may include various hardware, firmware and/or software attributes. The electronic controller 240 may be provided on a suitable electronics board 248. It will be understood that the illustrated electronic controller 240 may represent more than one processing device. For example, separate processing devices may be employed to interface with the gas and flow detecting components of the gas detection system 200 and operating components of the GC system 100, although such processing devices may communicate with each other via buses or other suitable communication links.

The gas detection system 200 also includes a suitable gas moving means such as a gas (or air) pump 252 that includes a pump inlet 254 and a pump outlet 256. The sample gas line 132 leading out from the GC oven 108 fluidly communicates with the pump inlet 254 to enable the gas detection system 200 to sample the gas (e.g., air) in the interior of the GC oven 108 at any desired instance of time. In some implementations, the gas pump 252 operates continuously during operation of the GC oven 108, thereby enabling continuous monitoring of the air inside the GC oven 108. The gas pump 252 may be controlled by the electronic controller 240 via an electrical line 258. The pump outlet 256 fluidly communicates with a gas detector 262 that includes an inlet 264 and an outlet 266, and with a flow detector 270. Although the flow detector 270 is schematically shown as including an inlet 272 and an outlet 274, in some implementations the flow detector 270 may be physically integrated in whole or in part with the gas detector 270 and measure flow based on temperature differentials, in which case the flow detector 270 may not require an inlet and outlet apart from those of the gas detector 262. The gas detector 262 and flow detector 270 may communicate with the electronic controller 240 via respective electrical lines 276 and 278 to provide the electronic controller 240 with measurement signals. From the gas detector 262 and flow detector 270, the sample gas may be conducted via an outlet 280 to any suitable destination.

The gas detector 262 may be any suitable device for detecting the presence and concentration of a combustible gas such as hydrogen, and the flow detector 270 may likewise be any suitable device for detecting the flow of the gas. In one example, the gas detector 262 may include a transducer in which resistance changes (e.g., decreases) in response to exposure to a combustible gas. For instance, the material utilized for the sensing element of the gas detector 262 may be a metal oxide semiconductor (MOS) material such as, for example, tin oxide ($SnO_2$), zinc oxide (ZnO), indium oxide ($In_2O_3$), tungsten oxide ($WO_3$), or the like. Such a gas detector 262 also may include a heating element such as an electrode to heat the sensor to a temperature value optimized for detecting a particular type of gas. For instance, in the case of hydrogen detection, the gas detector 262 may be heated to about 20° C. above ambient temperature upon startup of the gas detection system 200 and prior to sample gas flow. In this example, the flow detector 270 may be configured to measure the flow rate of the sample gas by monitoring the self-heating of the gas detector 262. To implement this technique, the flow detector 270 may include a temperature sensor mounted at or in close proximity to the gas detector 262 to measure the temperature of the gas detector 262, and another temperature sensor mounted at another, more remote location suitable for measuring the ambient temperature. After the gas detector 262 is initialized and the gas pump 252 is activated, the resulting sample gas flow cools down the gas detector 262. The differential between the respective temperatures of the gas detector 262 and the ambient environment may be correlated to the flow rate of the sample gas. Upon startup or during initialization of the gas detection system 200, the temperature to which the gas detector 262 is initially heated (e.g., about 20° C. above ambient temperature) may be stored in an appropriate memory device, such as may be located on the electronics board 248 and accessible by the electronic controller 240.

In some implementations, the gas detector 262 and the flow detector 270 may function solely as sensing devices, taking measurements and sending measurement-encoded signals to the electronic controller 240. In such implementations, the electronic controller 240 functions to receive the measurement signals, compare the measured values to preset minimum or maximum values, determine whether an error or alarm condition has occurred, and initiate an appropriate action response, examples of which are described below. In other implementations, the gas detector 262 and/or the flow detector 270 may include at least some logic or processing functionality. In these other implementations, the gas detector 262 and/or the flow detector 270 may also function to compare the measured values to preset minimum or maximum values (which in this case would be programmed into the gas detector 262 and/or the flow detector 270), and determine whether an error or alarm condition has occurred. In the case of an error or alarm condition, the signal or signals sent from the gas detector 262 and/or the flow detector 270 to the electronic controller 240 would include an indication of the error or alarm condition. In response to receipt of an error or alarm signal, the electronic controller 240 would then initiate the appropriate alarm response. Accordingly, as noted previously, the electronic controller 240 schematically illustrated in FIG. 2 may represent more than one processing device, and one or more of these processing device may be part of the gas detector 262 and/or the flow detector 270.

Figure 3:
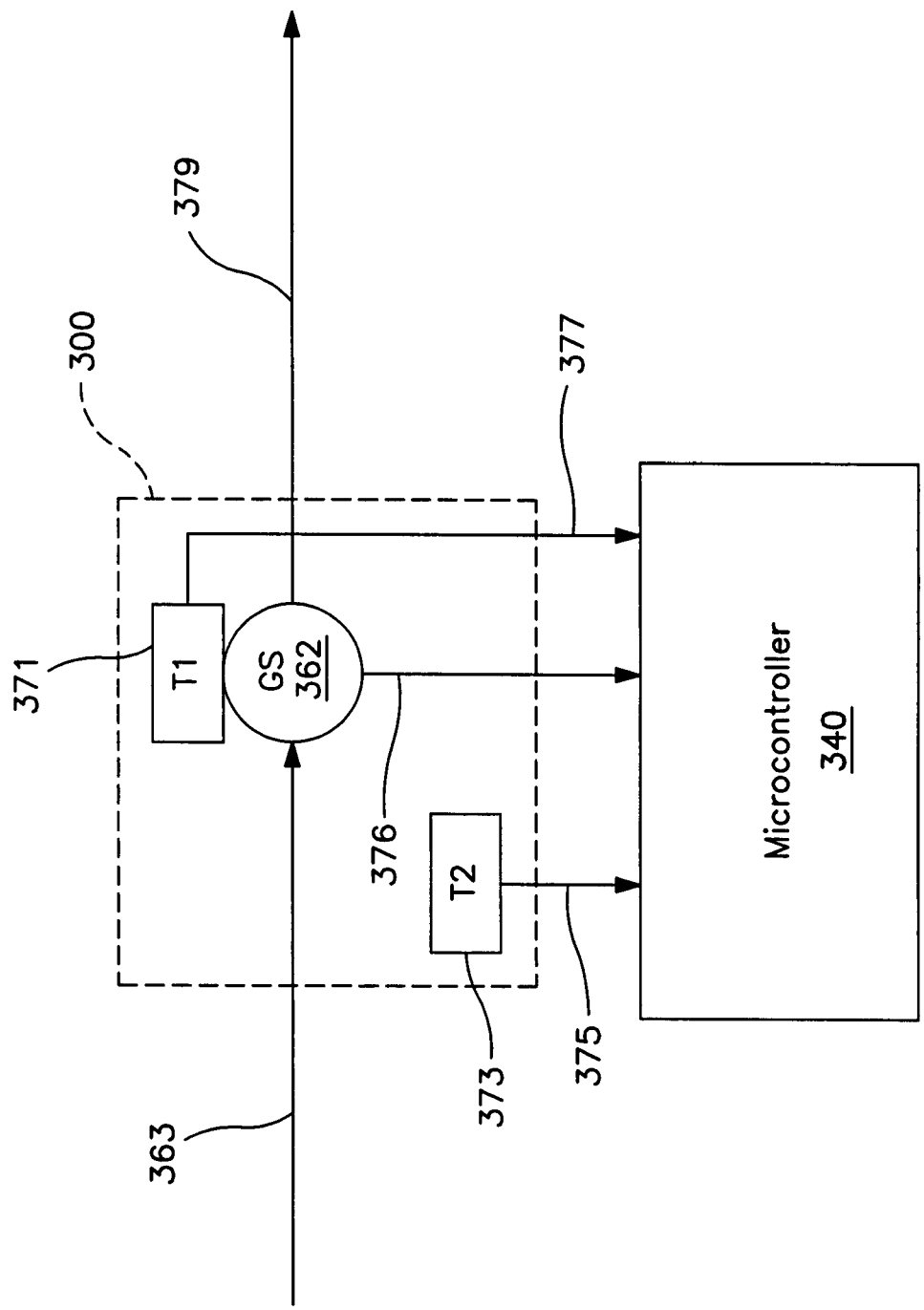
FIG. 3 is a schematic view of an example of a gas monitoring device or system according to one implementation of the invention.

FIG. 3 is a schematic view of an example of a gas monitoring device or system 300 according to one implementation of the invention. The gas monitoring device 300 may include both gas (presence and concentration) measurement/detection means and gas flow measurement/detection means. The gas monitoring device 300 may represent an example of the gas detector 262 and the flow detector 270 illustrated in FIG. 2. In FIG. 3, a sample gas input line 363 flows sample gas to a gas sensor 362, and a sample gas output line 379 carries discharged sample gas away from the gas sensor 362. The flow detecting portion of the gas monitoring device 300 includes a first temperature sensor 371 positioned at or near the gas sensor 362 to measure the temperature of the gas sensor 362, and a second temperature sensor 373 positioned remotely from the gas sensor 362 to measure ambient temperature. Measurement signals 375, 376 and 377 generated by the second temperature sensor 373, gas sensor 362, and first temperature sensor 371, respectively, are fed to a microcontroller 340 or other suitable controller. Accordingly, the gas monitoring device 300 may monitor gas concentration and flow as described by example above in conjunction with FIG. 2.

Referring back to FIG. 2, the gas detection system 200 may further include a means for conditioning the sampled gas prior to flowing the gas to the gas detector 262 and flow detector 270. In the illustrated example, the gas conditioning means is a heat exchanger or heat sink 282. In one implementation, the heat sink 282 includes a heat exchanging gas conduit 284 enclosed or formed in a housing or manifold 286. The gas conduit 284 fluidly interconnects the sample gas line 132 and the gas pump 252. In some implementations, the heat exchanging gas conduit 284 is coiled or serpentine so as to increase the surface area and time available for removing heat from the gas in the gas conduit 284. The length of the gas conduit 284, however, should be balanced against the desirability of minimizing the delay associated with conducting sample gas from the GC oven 108 to the gas detector 262 and flow detector 270. In some implementations, the manifold 286 is solid or partially solid for removing heat from the gas conduit 284 via a conduction mode prior to transfer to the ambient environment. In an alternative implementation, it may be desirable for the heat sink 282 to be configured to interface with a heat transfer medium circulation system (not shown). By this configuration, the manifold 286 would be partially hollow and a suitable heat exchanging medium or coolant such as water would be circulated through the manifold 286 and into thermal contact with the gas conduit 284, thereby enhancing the removal of heat from the gas in the gas conduit 284. In some implementations, the heat sink 282 may include a condensation drain 288 fluidly communicating with the gas conduit 284 to separate condensate from the cooled gas in the gas conduit 284, thus drying the gas prior to flowing to the gas detector 262 and flow detector 270. Depending on the type of gas detector 262 provided, including MOS-based sensors as described above, the removal of moisture and consequent lowering of humidity in the sample gas may improve the performance of the gas detector 262, such as by preventing loss of sensitivity and/or drift of sensor characteristics.

Figure 4:
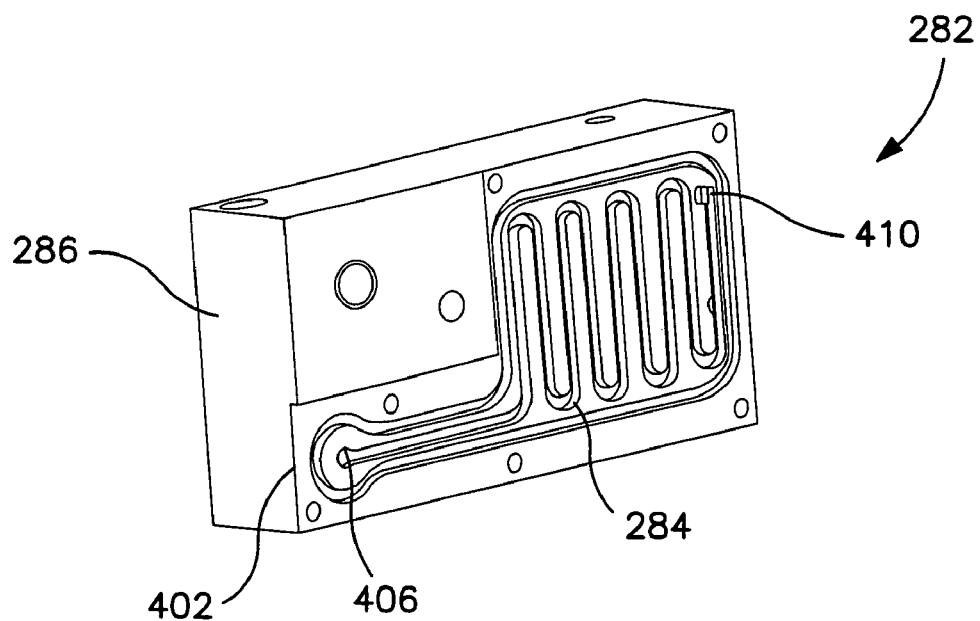
FIG. 4 is a perspective view of an example of a heat sink according to one implementation of the invention.
Figure 5:
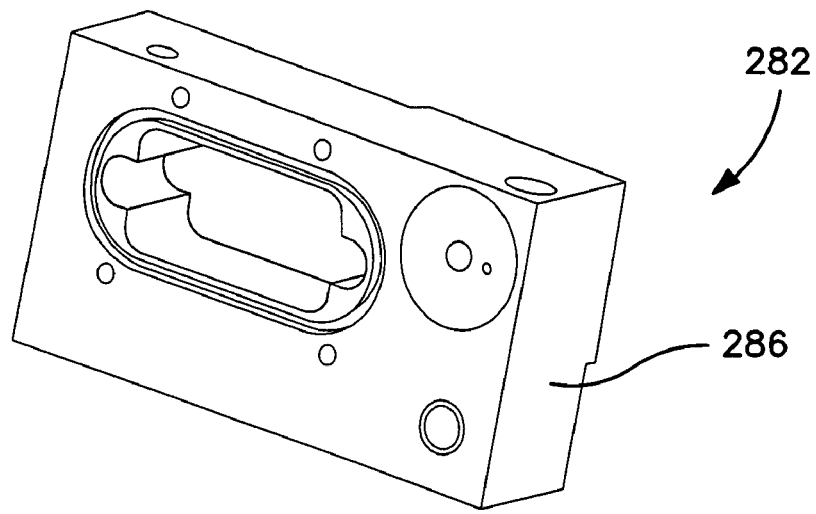
FIG. 5 is a perspective view of an opposite side of the heat sink illustrated in FIG. 4.

FIGS. 4 and 5 are perspective views of an example of the heatsink 282. As illustrated in FIG. 4, in this example the gas conduit 284 is milled as a channel in a mounting surface 402 of the manifold 286. The enclosure of the gas conduit 284 is completed by mounting the manifold 286 to a sheet (not shown) such as, for example, an instrument panel of the gas detection system 200. The opposing ends of the gas conduit 284 terminate at respective openings 406 and 410, one of which serves as the inlet into the gas conduit 284 while the other serves as the outlet.

Referring again to FIG. 2, the gas detection system 200 may further include one or more means for indicating the occurrence of an alarm or warning condition of the gas detection system 200. The recipients of such alarms or warning may be persons located in the vicinity and/or or remotely to the gas detection system 200. In the example illustrated in FIG. 2, an alarm indication device 292 communicates with the electronic controller 240 via an electrical line 294. Although in FIG. 2 only one alarm indication device 292 and one electrical line 294 are illustrated, it will be understood that these schematic elements may be representative of a plurality of different visual and/or audio alarm or warning devices such as, for example, beacons or lights (e.g., LEDs, lamps, etc.), electrical or electronic displays (e.g., CRTs, LCDs) located for example at a monitoring station, buzzers, beepers, horns, bells, loudspeakers, and the like.

An example of operation of the gas detection system 200 will now be described with reference being made primarily to FIG. 2. As an initial matter, operating parameters such as warning and alarm levels for the gas detector 262 and flow detector 270 are preset either by the user or by the provider of the gas detection system 200. Typically, the alarm level associated with the gas detector 262 will be set to a threshold value well below the LEL of the combustible gas being employed in the GC apparatus 100 (e.g., 40,000 ppm in the case of hydrogen). In addition to an LEL or sub-LEL alarm level that corresponds to meeting or exceeding the preset alarm threshold value, one or more warning levels may be set at selected percentages of the alarm level. The alarm level associated with the flow detector 270 will typically be set to a threshold low enough to ensure fail-safe operation of the gas detection system 200, because the gas detector 262 cannot accurately determine whether combustible gas is ramping up to a dangerous level in the GC oven 108 if the gas detector 262 is not receiving adequate sample gas flow. That is, the minimum flow rate value should be indicative of the occurrence of a problem such as failure of the gas pump 252, blockage in the flow path of the sample gas between the GC oven 108 and the gas detector 262, etc. Prior to startup of the GC apparatus 100, the gas detector 262 and/or flow detector 270 may need to be activated for a short time to provide a warm-up period and/or clear any initial transient conditions. In addition, the GC apparatus 100 is initialized as necessary for its proper operation.

Upon initialization of the GC apparatus 100 and the gas detection system 200, the GC apparatus 100 is activated in a conventional manner according to a desired experiment. Initially, the gas selection device 220 is switched to a state establishing a flow of combustible gas from the combustible gas supply source 204, through the combustible gas supply line 212, through the gas selection device 220, through the carrier gas supply line 120, and into the GC column 104 (FIG. 1) through which the selected combustible carrier gas transports the sample analytes of interest provided from the sample supply source 112 (FIG. 1). The initiation of the flow of combustible carrier gas into the GC column 104 may be synchronized to occur simultaneously or in close proximity with the activation of the gas pump 252, such that the GC apparatus 100 may immediately begin monitoring the air contained in the GC oven 108 for leakage of combustible gas. The electronic controller 240 may be programmed to coordinate these operations.

The activation of the gas pump 252 establishes a flow of sample gas from the GC oven 108 through the sample gas conduit 132, and through the gas conduit 284 of the heat sink 282 where the sample gas is conditioned as described above. The flow of sample gas continues through the pump 252 and through the gas detector 262 (and, depending on the design of the flow detector 270, through the flow detector 270 as well), and is exhausted via the outlet 280 to an appropriate destination. While the sample gas is flowing, the electronic controller 240 samples signal-encoded measurements outputted from the gas detector 262 and flow detector 270 on a continuous or frequent basis and thereby checks for warning and alarm conditions throughout the operation of the GC apparatus 100. If desired, gas concentration and flow rate may be displayed at a monitoring station (not shown), as well as other measurements such as gas temperature, pressure, and parameters and measurements related to running the GC experiment.

The electronic controller 240 may be programmed to compare each measurement value sampled from the gas detector 262 and from the flow detector 270 to the corresponding preset values for maximum gas concentration and minimum flow rate. If the actual measured gas concentration value meets or exceeds the preset threshold value, the electronic controller 240 sends a control signal to the gas selection device 220 to switch to a state that cuts off the flow of combustible gas and establishes a flow of safe gas from the safe gas supply source 208 to the GC column 104 (FIG. 1) via the safe gas supply line 216 and carrier gas supply line 120. The dangerous condition of excessive combustible gas in the GC oven 108 is eliminated through continued operation of the gas pump 252, which purges the GC oven 108 of the leaked combustible gas and routes this gas to the outlet 280. Similarly, if the actual measured sample gas flow rate fails to exceed, reaches, or falls below the predetermined minimum flow rate, the electronic controller 240 switches the gas selection device 220 to the safe gas flow state. In the case of either excessive combustible gas concentration or inadequate flow rate, the electronic controller 240 may activate the alarm indicator or indicators 292 and provide error indications as desired. The gas detection system 200 may be configured so as to require the alarms to be reset by user intervention. The gas detection system 200 may also be configured to shut down the GC system 100 in response to one or more repeated occurrences of an alarm or error condition.

Figure 6:
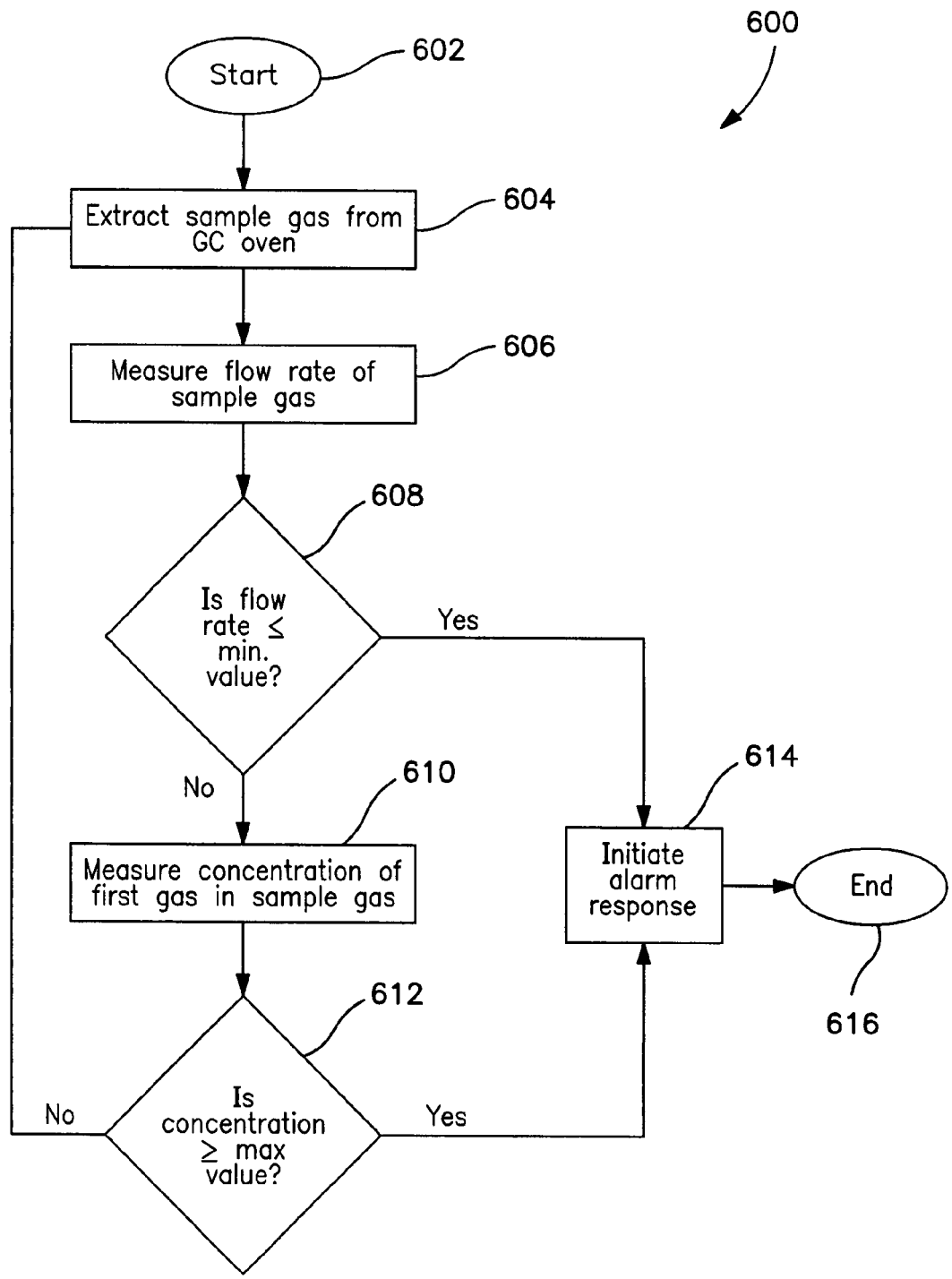
FIG. 6 is a flow diagram illustrating an example of a method for detecting gas according to one implementation of the invention.

FIG. 6 is a flow diagram 600 illustrating an example of a method for detecting or monitoring gas. The flow diagram 600 may also represent an apparatus or system capable of performing the illustrated method. The method begins at the starting point 602. Upon the startup of a GC oven, at block 604, sample gas (e.g., air or a mixture of air and possibly other components) is extracted from the GC oven. At block 606, the flow rate of the sample gas is measured. At decision block 608, a determination is made as to whether the flow rate of the sample gas equals or is less than a minimum value. If the flow rate is above the minimum value, the flow rate is considered to be proper and the process advances to block 610. At block 610, the gas concentration of a first gas in the sample gas is measured. In this example, a "first" gas is a combustible gas such as hydrogen that may be a component of the sample gas extracted from the GC oven. Accordingly, measuring the concentration of the first gas may entail operating a gas detection device adapted to be sensitive to exposure to the first gas. At decision block 612, a determination is made as to whether the concentration of the first gas equals or is greater than a maximum value. If the concentration is less than the maximum value, the concentration of the first gas is considered to be at a safe level, which of course may be zero in the case of an absence of the first gas in the sample gas. The process then returns to block 604.

It will be understood that the loop or cycle illustrated in FIG. 6 that includes blocks 604, 606, 608, 610 and 612 may represent a continuous process. That is, extracting the sample gas from the GC oven may constitute establishing a continuous flow of the sample gas out from the GC oven. The flow rate of the sample gas and the concentration of the first gas may be monitored on a continuous basis. Moreover, the continuous performance of these method steps may produce flow rate and concentration measurements on an essentially continuous or high frequency basis. Hence, the determinations as to whether the flow rate and concentration are acceptable may likewise be made on an essentially continuous basis. The determinations may be made each time updated measurement data are generated. It also follows that the order of the blocks 604, 606, 608, 610 and 612 illustrated in FIG. 6 is arbitrary. The measurements may be performed simultaneously or at least in no particular order. Likewise, the determinations based on the measurements may be performed simultaneously or at least in no particular order. On the other hand, the monitoring of the flow rate of the sample gas depicted by blocks 606 and 608 may be considered as ensuring that the monitoring of the gas concentration depicted by blocks 610 and 612 is a fail-safe or accurate operation. This is because the monitoring of the gas concentration requires an adequate flow rate of sample gas.

Continuing with the method illustrated in FIG. 6, if at decision block 608 a determination is made that the flow rate of the sample gas equals or is less than the minimum value, and/or if at decision block 612 a determination is made that the concentration of the first gas in the sample gas equals or is greater than the maximum value, the process advances to block 614 where an appropriate alarm response is initiated. Examples of alarm responses are described above, and may include ceasing the flow of the first gas to the GC oven and switching over to flowing a second gas to the GC oven, activating a visual or audio alarm indicator, or the like. In this example, the "second" gas is a gas considered to be a safe gas or at least safer than the first gas (e.g., less combustible or non-combustible), such as helium or nitrogen. After the alarm response has been initiated, the process may end at ending point 616, which may entail requiring a user to reset the alarm and one or more other components of the system in which the illustrated method is being implemented. The process may also return to the starting point 602 for continued implementation of the method in conjunction with the same GC experimental run or a subsequent run.

As noted above, FIG. 6 may represent an example of an apparatus or system 600 for performing the illustrated method. Accordingly, the blocks 604-614 may be considered as depicting one or more means for performing the functions or steps corresponding to those blocks 604-614 and just described. Examples of systems, apparatus and devices capable of implementing these functions are described above in conjunction with FIGS. 1-5.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A gas detection system, comprising:
    a gas chromatograph (GC) oven;
    a self-heating gas detector;
    a sample gas moving device fluidly interposed between the GC oven and the gas detector; and
    a flow detector including circuitry for monitoring the self-heating of the gas detector.

2. The system of claim 1, further including a sample gas cooling device fluidly interposed between the GC oven and the sample gas moving device, the cooling device including a condensation drain.

3. The system of claim 1, further including an electronic controller in signal communication with the gas detector and the flow detector, the electronic controller including circuitry for comparing a signal received from the gas detector indicative of measured gas concentration with a maximum gas concentration value, and for comparing a signal received from the flow detector indicative of measured gas flow rate with a minimum flow rate value.

4. The system of claim 3, further including a carrier gas selecting device in signal communication with the electronic controller, the carrier gas selecting device including a carrier gas outlet fluidly communicating with the GC oven, a first gas inlet, and a second gas inlet, wherein, in response to the electronic controller determining that the measured gas concentration is equal to or greater than the maximum gas concentration value or that the measured gas flow rate is equal to or less than the minimum flow rate value, the selecting device is switchable between a first state at which a first gas flows from the first gas inlet to the GC oven and a second state at which a second gas flows from the second gas inlet to the GC oven.

5. The system of claim 1, further including:
    a first gas supply;
    a second gas supply;
    a carrier gas selecting device including an outlet fluidly communicating with the GC oven, a first inlet fluidly communicating with the first gas supply, and a second inlet fluidly communicating with the second gas supply, wherein the carrier gas selecting device is switchable between a first state at which a first gas flows from the first gas supply to the GC oven and a second state at which a second gas flows from the second supply to the GC oven; and
    an electronic controller in signal communication with the gas detector, the flow detector and the carrier gas selecting device, the controller including circuitry for switching the carrier gas selecting device from the first state to the second state in response to the gas detector detecting an excessive concentration of the first gas or a insufficient flow rate of gas to the gas detector.

6. The system of claim 1, wherein the flow detector includes a first temperature sensor positioned at the gas detector and a second temperature sensor positioned remotely from the gas detector.

7. A gas detection system, comprising:
    a gas chromatograph (GC) oven;
    a gas detector;
    a sample gas device fluidly interposed between the GC oven and the gas detector;
    a flow detector;
    means for receiving a flow measurement signal from the flow detector indicative of the flow rate of a sample gas flowing from the GC oven to the gas detector, and for determining whether the value of the flow measurement signal is less than or equal to a minimum flow rate value; and
    means for switching from flowing a first gas into the GC oven to flowing a second gas into the GC oven in response to the value of the flow measurement signal being less than or equal to the minimum flow rate value.

8. The system of claim 7, further including a sample gas cooling device fluidly interposed between the GC oven and the sample gas moving device, the cooling device including a condensation drain.

9. The system of claim 7, wherein the receiving and determining means includes an electronic controller in signal communication with the flow detector.

10. The system of claim 7, wherein the switching means includes a gas selecting device in signal communication with the receiving and determining means, the gas selecting device including an outlet fluidly communicating with the GC oven, a first gas inlet, and a second gas inlet.

11. The system of claim 7, further including means for receiving a concentration measurement signal from the gas detector indicative of the concentration of the first gas in the sample gas flowing from the GC oven to the gas detector, and for determining whether the value of the concentration measurement signal is equal to or greater than a maximum gas concentration value, wherein the switching means includes means for switching from flowing the first gas into the GC oven to flowing the second gas into the GC oven in response to the value of the concentration measurement signal being equal to or greater than the maximum gas concentration value.

12. The system of claim 11, wherein the means for receiving the concentration measurement signal and for determining whether the value of the concentration measurement signal is equal to or greater than a maximum gas concentration value includes an electronic controller in signal communication with the gas detector.

13. The system of claim 7, wherein the flow detector includes a first temperature sensor positioned at the gas detector and a second temperature sensor positioned remotely from the gas detector.

14. A method for detecting a gas during a gas chromatographic (GC) process, comprising:
flowing a sample gas from a GC oven;
determining whether a concentration of a first gas in the sample gas equals or exceeds a maximum gas concentration value;
determining whether the flow rate of the sample gas equals or is less than a minimum flow rate value; and
if either the first gas equals or exceeds the maximum gas concentration value or the flow rate equals or is less than the minimum flow rate value, initiating an alarm response.

15. The method of claim 14 further including, after flowing the sample gas from the GC oven, conditioning the sample gas by cooling and removing condensate from the sample gas, and flowing the conditioned sample gas to a gas detector.

16. The method of claim 14, wherein determining whether the concentration of the first gas in the sample gas equals or exceeds a maximum gas concentration value includes flowing the sample gas from the GC oven to a self-heating gas detector, and determining whether the flow rate of the sample gas equals or is less than a minimum flow rate value includes measuring a temperature of the self-heating gas detector.

17. The method of claim 14, further including flowing the first gas to the GC oven, wherein initiating the alarm response includes ceasing flow of the first gas to the GC oven and flowing a second gas to the GC oven.

18. The method of claim 14, wherein initiating the alarm response includes switching a gas selection device from a first state in which the first gas flows to the GC oven to a second state in which a second gas flows to the GC oven.

19. The method of claim 14, wherein initiating the alarm response includes activating an alarm indicator.

20. The method of claim 14, further including flowing the first gas into a GC column in the GC oven.

* * * * *